United States Patent
Abels et al.

(10) Patent No.: US 7,063,530 B2
(45) Date of Patent: **\*Jun. 20, 2006**

(54) SELF-LIGATING ORTHODONTIC BRACKETS COMPRISING A FILLED AND FIBER-REINFORCED POLYMERIC MATERIAL

(76) Inventors: Norbert Abels, Alleestrasse 30a, 66424 Homburg (DE); Claus-H. Backes, St. Wendeler Strasse 45, 66113 Saarbrücken (DE)

(\*) Notice: Subject to any disclaimer, the term of this patent is extended or adjusted under 35 U.S.C. 154(b) by 0 days.

This patent is subject to a terminal disclaimer.

(21) Appl. No.: 11/071,783

(22) Filed: Mar. 3, 2005

(65) Prior Publication Data

US 2005/0244773 A1  Nov. 3, 2005

Related U.S. Application Data

(63) Continuation-in-part of application No. 10/835,744, filed on Apr. 30, 2004.

(51) Int. Cl.
*A61C 3/00* (2006.01)
(52) U.S. Cl. .......................................... 433/8
(58) Field of Classification Search ............... 433/8–17
See application file for complete search history.

(56) References Cited

U.S. PATENT DOCUMENTS

| | | | |
|---|---|---|---|
| 4,717,341 A | 1/1988 | Goldberg et al. | 433/9 |
| 4,894,012 A | 1/1990 | Goldberg et al. | 433/215 |
| 5,078,596 A | 1/1992 | Carberry et al. | 433/8 |
| 5,707,231 A * | 1/1998 | Watt et al. | 433/8 |
| 5,857,849 A | 1/1999 | Kurz | 433/10 |
| 6,607,383 B1 | 8/2003 | Abels et al. | 433/11 |
| 6,616,445 B1 | 9/2003 | Abels et al. | 433/11 |
| 6,960,080 B1 * | 11/2005 | Abels et al. | 433/10 |
| 6,960,081 B1 * | 11/2005 | Abels et al. | 433/10 |
| 2002/0110771 A1 | 8/2002 | Abels et al. | 433/10 |
| 2002/0110772 A1 | 8/2002 | Abels et al. | 433/10 |
| 2002/0110773 A1 | 8/2002 | Abels et al. | 433/10 |
| 2002/0110774 A1 | 8/2002 | Abels et al. | 433/10 |
| 2002/0110775 A1 | 8/2002 | Abels et al. | 433/11 |
| 2002/0110778 A1 | 8/2002 | Abels et al. | 433/11 |
| 2002/0187452 A1 | 12/2002 | Abels et al. | 433/11 |
| 2003/0049582 A1 | 3/2003 | Abels et al. | 433/11 |

\* cited by examiner

*Primary Examiner*—John J. Wilson
*Assistant Examiner*—Meoghan E. MacPherson
(74) *Attorney, Agent, or Firm*—Workman Nydegger

(57) ABSTRACT

A self-ligating orthodontic bracket includes a bracket base, an arch wire slot in the bracket base, and a ligation cover. The bracket base and the ligation cover comprise a polymer resin reinforced glass or ceramic fibers, and further comprising a particulate filler. The cover is hingedly connected to the bracket base and rotatable relative to the bracket base between an open, non-ligating position and a closed, ligating position. The combination of reinforcing fibers and filler (e.g., spherical glass particles) provides substantially increased overall strength and durability while providing increased flexibility and toughness in the region of an optional hinge connection between the ligation cover and the bracket base.

20 Claims, 4 Drawing Sheets

SELF-LIGATING ORTHODONTIC BRACKETS COMPRISING A FILLED AND FIBER-REINFORCED POLYMERIC MATERIAL

RELATED APPLICATIONS

The present application is a continuation-in-part of U.S. patent application Ser. No. 10/835,744, filed Apr. 30, 2004 and entitled "SELF-LIGATING ORTHODONTIC BRACKETS COMPRISING A FIBER-REINFORCED POLYMERIC MATERIAL," which is hereby incorporated by reference in its entirety.

BACKGROUND OF THE INVENTION

1. The Field of the Invention

The present invention is in the field of orthodontic brackets, more particularly to self-ligating orthodontic brackets that include a bracket base, at least one slot for receiving an arch wire, and a ligation cover. Such brackets comprise a fiber and/or particle-reinforced polymer material designed for self-ligating brackets.

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth to correct underbites or overbites. For example, orthodontic treatment can improve the patient's occlusion, or enhanced spatial matching of corresponding teeth.

The most common form of orthodontic treatment involves the use of orthodontic brackets and wires, which together are commonly referred to as "braces." Orthodontic brackets, more particularly the orthodontic bases, are small slotted bodies configured for direct attachment to the patient's teeth or, alternatively, for attachment to bands which are, in turn, cemented or otherwise secured around the teeth. Once the brackets are affixed to the patient's teeth, such as by means of glue or cement, a curved arch wire is inserted into the slot of each bracket. The arch wire acts as a template or track to guide movement of the teeth into proper alignment.

There are two distinct classes of orthodontic brackets: those that require the use of ligatures to fasten the arch wire to the bracket, and those that are self-ligating. In brackets of the first type, small ligature wires or elastic bands are typically used to hold the arch wire in a securely seated position in the brackets. Ligatures or some other form of fastening means are essential to ensure that the tensioned arch wire is properly positioned around the dental arch, and to prevent the wire from being dislodged from the bracket slots during chewing of food, brushing of teeth, or application of other forces. One type of commercially available ligature is a small, elastomeric O-ring, which is installed by stretching the O-ring around small wings known as "tie wings" that are connected to the bracket body. Metal ligatures are also used to retain arch wires within the bracket slots.

In an effort to simplify the process of installing braces, a variety of self-ligating brackets have been developed. The term "self-ligating bracket" refers to a class of orthodontic brackets that include some sort of cover, whether separate from or hingedly or slidably attached to the base, which encloses or otherwise retains the arch wire within the slot of the base. Examples of self-ligating brackets are disclosed in U.S. Pat. Nos. 3,748,740, 4,077,126, 5,857,849, and 6,071,118.

Self-ligating brackets have grown in popularity because of their convenient features, but they still exhibit certain disadvantages, not least of which is that they can be rather fragile if made from polymers. In addition, many polymers can deform (or "creep") over time, especially when the constant force from an arch wire is applied thereto. Metal brackets are strong, but have the distinct disadvantage of being less attractive and providing sharp, jagged, or hard edges that can cause injury.

Therefore, there exists a need for designs and materials that impart increased strength and durability to polymeric self-ligating brackets, while also being easy to open and close and easy and inexpensive to manufacture and install.

BRIEF SUMMARY OF THE PREFFERED EMBODIMENTS

Generally, the orthodontic brackets of the present invention include a bracket base, an arch wire slot in the bracket base, and a ligation cover. The cover is hingedly connected to the bracket base and rotatable about the hinge relative to the bracket base between an open, non-ligating position and a closed, ligating position. The bracket base and the ligation cover comprise a polymer resin composition reinforced with TFG Type 3 glass ("c-glass") or other appropriate fibers and/or filler particles, such as spherical glass particles.

The orthodontic bracket is preferably formed as one single piece, requiring no assembly. This reduces the cost and complexity of manufacture and prevents unwanted separation of the bracket parts. Although other methods may be used, low cost manufacture is possible by forming the bracket by injection molding.

The brackets of the present invention are self-ligating, i.e., the arch wire is clamped or otherwise held between the ligation cover and the bracket base. According to one embodiment, the ligation cover is attached to the base by an elongate film hinge. The cover is rotatable about the film hinge relative to the bracket base between an open, non-ligating position relative to the arch wire slot and a closed, ligating position relative to the arch wire slot. According to one embodiment, a curved hinge guide structure may operate in conjunction with the film hinge to improve the functionality of the bracket. In addition to or instead of the curved structure, a camming structure may be provided that biases the ligation cover toward the open, non-ligating position when the ligation cover is not latched relative to the bracket base. The ligation cover may advantageously include a latch member that interacts with a corresponding recess of the bracket base in order to selectively lock and unlock the cover relative to the base.

An elongate film hinge is characterized by its ability to distribute forces and stresses associated with operation of the hinge along a significant portion of its entire length. This is in contrast to other types of film hinges where the forces and stresses are concentrated at one point or line, which can create a localized area where the film hinge is more radically stressed and can more easily break. The result is an improved film hinge that can resist breakage when exposed to shearing and bending forces, such as may occur during placement and use of the orthodontic brackets.

Forming the bracket base and ligation cover of a polymer resin composition reinforced with c-glass fibers provides increased flexibility, toughness, and resilience. These characteristics are particularly beneficial in the area of the hinge(s) connecting the ligation cover to the bracket base. Reinforcement with c-glass fibers, which are characterized by relatively small diameters, high flexibility, and short fiber length, results in substantial improvement of flexibility, toughness, and resilience as compared to reinforcement with other materials. Maintaining flexibility of the polymeric material, while providing increased strength and resistance to creep, is particularly beneficial in the case where an orthodontic bracket includes a living hinge (e.g., a film hinge) that is expected to flex back and forth several, and often numerous, times during the lifespan of the bracket.

According to one embodiment, reinforcing c-glass fibers are preferably included in an amount in a range of about 10% to about 50% by weight of the fiber-reinforced polymer resin composition, more preferably in a range of about 15% to about 40% by weight, and most preferably in a range of about 20% to about 35% by weight.

According to one embodiment, the reinforcing c-glass fibers preferably have a fiber length less than about 500 microns, more preferably less than about 200 microns, and most preferably less than about 100 microns.

According to one embodiment, the reinforcing c-glass fibers preferably have a fiber diameter in a range of about 0.5 to about 10 microns, more preferably in a range of about 1 to about 6 microns, and most preferably in a range of about 2 to about 4 microns.

According to one embodiment, the reinforcing c-glass fibers preferably have an aspect ratio in a range of about 5 to about 200, more preferably in a range of about 10 to about 100, and most preferably in a range of about 20 to about 50.

In addition to, or instead of c-glass fibers, the fiber-reinforced polymer resin compositions may include other types of glass or ceramic fibers having similar characteristics of length, diameter and aspect ratio.

The polymeric resin may comprise one or more suitable thermoplastic or thermoset resins, including amorphous polymers, crystalline polymers, or a blend of both. Examples of suitable amorphous polymers that may be reinforced with fibers and used to manufacture self-ligating orthodontic brackets include, but are not limited to amorphous polyamides (e.g., GRILAMID nylon), acetal polymers, polyetherimides, and polycarbonates. Examples of suitable crystalline polymers include, but are not limited to, polyarylether ketones (PEEK) and crystalline polyamides (e.g., TROGAMID nylon).

In addition, the ligation cover may optionally include a bearing protrusion that aligns with or extends partially into the arch wire slot so as to provide force when the cover is closed in a manner so that the bearing protrusion fixes the arch wire.

According to one embodiment, the polymeric material may also include a particulate filler that further reinforces the orthodontic bracket. Forming the bracket base and ligation cover of a polymer resin composition that includes both reinforcing c-glass fibers and a filler (e.g., spherical glass particles) provides even further increased flexibility, toughness, and resilience. These characteristics are particularly beneficial in the area of the hinge(s) connecting the ligation cover to the bracket base. Inclusion of both glass particle filler and c-glass reinforcing fibers results in substantial improvement of flexibility, toughness, and resilience throughout the bracket, and particularly to the hinge area, which requires flexibility and resilience, and the area surrounding the arch wire slot, which requires toughness and durability. Other exemplary filler particles include ceramic particles, ceramic/glass particles, and organically modified ceramic particles (e.g., Ormocer).

According to one embodiment, the filler is preferably included in an amount in a range of about 1% to about 30% by weight of the polymer resin composition, more preferably in a range of about 2% to about 20% by weight, and most preferably in a range of about 5% to about 10% by weight.

According to one embodiment, the filler preferably has an average particle diameter in a range of about 0.3 to about 30 microns, more preferably in a range of about 0.5 to about 20 microns, and most preferably in a range of about 1 to about 10 microns.

According to one embodiment, the combined total glass content (reinforcing c-glass fibers plus filler) preferably ranges from about 10% to about 65% by weight of the filled and fiber-reinforced polymer resin composition, more preferably in a range of about 30% to about 55% by weight, and most preferably in a range of about 40% to about 50% by weight.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

Figure 1A:
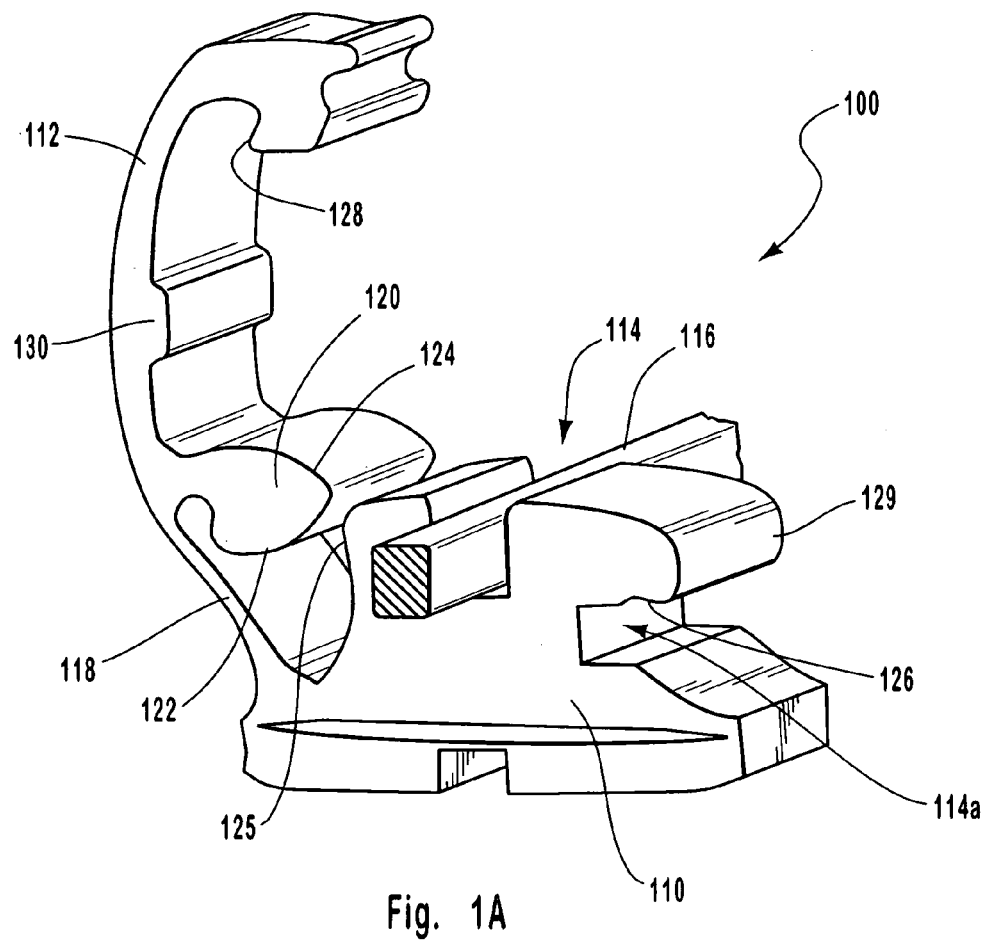
FIGS. 1A–1B illustrate an exemplary self-ligating orthodontic bracket that can be formed from a polymer resin reinforced with c-glass fibers and/or glass particles.

The orthodontic brackets of the present invention include a bracket base, an arch wire slot in the bracket base, and a ligation cover. The cover is hingedly connected to the bracket base and rotatable relative to the bracket base between an open, non-ligating position and a closed, ligating position. The bracket base and the ligation cover comprise a polymer resin reinforced with c-glass fibers.

II. Reinforcement With C-Glass Fibers

Forming the bracket base and ligation cover from a polymer resin reinforced with c-glass fibers results in an orthodontic bracket having increased strength and durability, while exhibiting toughness and flexibility in the region of the hinge connecting the ligation cover to the bracket base. Toughness and flexibility are important characteristics for a hinged cover of a self-ligating bracket. Strength and durability are especially useful for the bracket base, particularly the area of the base surrounding the arch wire slot. Increased strength and durability helps prevent such an area from becoming deformed or damaged due to forces transmitted by the arch wire to the arch wire slot. Forming the bracket base and ligation cover from a polymer resin reinforced with c-glass fibers results in increased strength and durability while exhibiting toughness and flexibility in the region of the hinge as compared to brackets reinforced with other materials.

C-glass fibers are a preferred class of glass fibers used to reinforce the polymer resins in forming an orthodontic bracket. C-glass fibers are characterized by relatively small diameters, great flexibility, and short fiber length. Reinforcement with c-glass fibers results in substantial improvement of flexibility and toughness as compared to reinforcement with other materials. One example of a suitable c-glass fiber is FAMIX 1103-B1, manufactured by Osthoff-Petrasch, located in Germany.

According to one embodiment, the c-glass fibers may be coated with an amino-silane coating, which makes them more compatible when blended with thermoplastic polymers. FAMIX 1103-B1 is especially formulated for reinforcement within adhesives, plastics, sealants, and resin-based products. When mixed with a molten thermoplastic polymer, slow, forceful stirring should be maintained while avoiding strong shear forces which might cause shortening of the glass fibers.

The physical and chemical properties of FAMIX 1103-B1 are as follows:

| Color | White |
|---|---|
| Density | 2.5 g/cc |
| Fiber diameter | 3.0–3.2 microns |
| Fiber length | less than 100 microns |
| Softening temperature | 700° C. |
| Application temperature | 500° C. |
| Moisture content | less than 0.3% |
| Silane content | 0.3–0.5% |

| Analysis Data | Weight Percent |
|---|---|
| $SiO_2$ | 63–66 |
| CaO | 4–6 |
| $Al_2O_3$ | 4–5 |
| $Fe_2O_3$ | 0.43 |
| $B_2O_3$ | 3–6 |
| $Na_2O$ | 11–14 |
| $K_2O$ | 1.30 |

According to one embodiment, the reinforcing c-glass fibers are preferably included in an amount of in a range of about 10% to about 50% by weight of the fiber-reinforced polymer resin composition, more preferably in a range of about 15% to about 40% by weight, and most preferably in a range of about 20% to about 35% by weight.

According to one embodiment, the reinforcing c-glass fibers preferably have a fiber length less than about 500 microns, more preferably less than about 200 microns, and most preferably less than about 100 microns.

According to one embodiment, the reinforcing c-glass fibers preferably have a fiber diameter in a range of about 0.5 to about 10 microns, more preferably in a range of about 1 to about 6 microns, and most preferably in a range of about 2 to about 4 microns.

According to one embodiment, the reinforcing c-glass fibers preferably have an aspect ratio in a range of about 5 to about 200, more preferably in a range of about 10 to about 100, and most preferably in a range of about 20 to about 50.

Other components, such as fillers, flow additives, and other components known in the art may be added, as desired.

In addition to, or instead of c-glass fibers, the fiber-reinforced polymer resin compositions may include other types of glass or ceramic fibers having similar characteristics of length, diameter and aspect ratio.

III. Reinforcement With C-Glass Fibers and a Filler

According to one embodiment, the polymeric material may also or instead include a filler that further reinforces the orthodontic bracket. Forming the bracket base and ligation cover from a filled polymer resin reinforced with c-glass fibers results in an orthodontic bracket having further increased strength and durability, while also exhibiting toughness and flexibility in regions where those characteristics are advantageous (e.g., an optional hinge connecting the ligation cover to the bracket base). Strength and durability are especially useful for the bracket base, particularly the area of the base surrounding the arch wire slot. Increased strength and durability helps prevent such an area from becoming deformed or damaged due to forces transmitted by the arch wire to the arch wire slot. Forming the bracket base and ligation cover from a polymer resin that is reinforced with both c-glass fibers and a spherical glass particle filler results in further increased strength and durability while exhibiting toughness and flexibility in the region of an optional hinge as compared to brackets reinforced only with c-glass fibers.

Spherical glass particles are a preferred type of filler used to further reinforce the polymer resins used in forming an orthodontic bracket. Reinforcement with both c-glass fibers and glass particles results in substantial improvement of flexibility, toughness, strength and durability as compared to reinforcement with other materials or only with c-glass. Since filler particles typically do not increase the strength and flexibility of materials to which they are added, the fact that glass particles do when added to polymers used to manufacture orthodontic brackets is a surprising and unexpected result. Two examples of suitable glass fillers include GM27884 and G018–053, both manufactured by SCHOTT, located in Germany.

According to one embodiment, the glass particle filler may also be coated with an amino-silane coating, which makes them more compatible when blended with thermoplastic polymers. The physical and chemical properties of GM27884 and G018–053 are as follows:

|  | GM27884 | G018–053 |
|---|---|---|
| Index of Refraction | 1.53 | 1.53 |
| Density (g/cm³) | 2.8 | 2.9 |
| Transformation Temp. (° C.) | 630 | 595 |
| Radio Opacity (mm) | 4.2 | 4.8 |

| Analysis Data | Weight Percent | Weight Percent |
|---|---|---|
| $SiO_2$ | ~55 | ~50 |
| BaO | ~25 | ~30 |
| $B_2O_3$ | ~10 | ~10 |
| $Al_2O_3$ | ~10 | ~10 |
| F | — | ~2 |

Other fillers that may be used include, but are not limited to ceramic particles, glass/ceramic particles, or organically modified ceramic particles (e.g., Ormocer), any of which are preferably spherical.

According to one embodiment, the filler is preferably included in an amount in a range of about 1% to about 30% by weight of the fiber-reinforced and filled polymer resin composition, more preferably in a range of about 2% to about 20% by weight, and most preferably in a range of about 5% to about 10% by weight.

According to one embodiment, the filler preferably has an average (i.e., $d_{50}$) particle diameter in a range of about 0.3 to about 30 microns, more preferably in a range of about 0.5 to about 20 microns, and most preferably in a range of about 1 to about 10 microns.

Including a glass particle filler within the fiber reinforced polymer resin composition allows the orthodontic brackets to have a higher total glass content (resulting in greater strength and durability in the region of the arch wire slot) without an expected decrease in toughness and flexibility in the region of an optional hinge. Surprisingly, it has been found that toughness and flexibility increases at the same time that strength and durability increases.

According to one embodiment, the combined total glass content (reinforcing c-glass fibers plus glass spherical particle filler) preferably ranges from about 10% to about 65% by weight of the filled and fiber-reinforced polymer resin composition, more preferably in a range of about 30% to about 55% by weight, and most preferably in a range of about 40% to about 50% by weight.

IV. Exemplary Polymeric Resin Materials

The polymeric resin may comprise one or more suitable thermoplastic or thermoset resins, including amorphous polymers, crystalline polymers, or a blend of both. Examples of suitable amorphous polymers that may be reinforced with fibers (and optionally a filler) and used to manufacture self-ligating orthodontic brackets include, but are not limited to amorphous polyamides (e.g., GRILAMID nylon, manufactured by EMS-CHEMIE AG, located in Germany), acetal polymers, polyetherimides, and polycarbonates. Examples of suitable crystalline polymers include, but are not limited to, polyarylether ketones (PEEK) and crystalline polyamides (e.g., TROGAMID nylon, manufactured by Degussa AG, located in Germany).

V. Exemplary Orthodontic Brackets

A polymer resin reinforced with c-glass fibers (and optionally a filler) may be used to form a self-ligating orthodontic bracket of any design. The following examples are to be considered in all respects only as illustrative and not restrictive. They are intended to give a general understanding of some applications of the present invention.

Figure 1B:
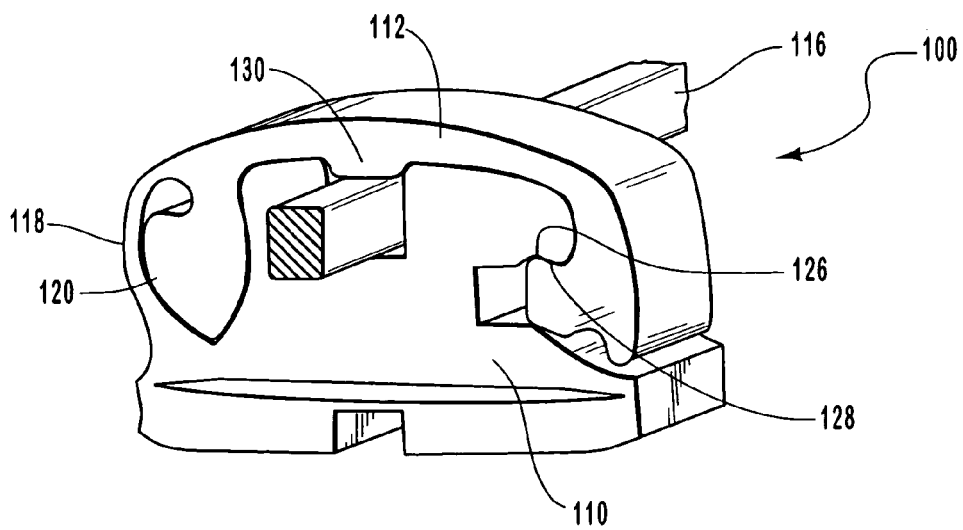

The orthodontic bracket shown in FIGS. 1A–1B may be manufactured in one single piece as an injection molded plastic part from a polymer resin reinforced with c-glass fibers (and optionally a filler). The orthodontic bracket 100 has a bracket base 110 to which a ligation cover 112 is hingedly attached. A slot 114 open to the upper side of the bracket base 110 is provided near the center of said bracket base 110 and serves for the insertion of an arch wire 116 therein. An additional arch wire slot 114a may also be provided. The arch wire 116, shown with a square cross-section (any other cross section known in the art could be used), is arranged inside the slot 114 and serves to correct tooth alignment in a known manner.

The ligation cover 112 is hingedly connected to the bracket base 110 by an elongate film hinge 118. The ligation cover 112 is such that it may be selectively rotated between an open and a closed position relative to the arch wire slot 114, with the ligation cover, maintaining the arch wire 16 within the slot 114 when the ligation cover 112 is in the closed, ligating position. The elongate film hinge 118 preferably has a length and thickness that are selected so that the hinge 118 has a desired level of flexibility and toughness. Forming the bracket of a polymer resin reinforced with c-glass fibers provides overall increased strength and durability while providing increased flexibility and toughness in the region of the elongate film hinge 118 as compared to brackets with no fiber reinforcement or reinforcement with fibers that are substantially stiffer and more rigid than c-glass fibers. Forming the bracket of a polymer resin reinforced with both c-glass fibers and a glass particle filler provides even further increased flexibility, toughness, strength, and durability.

The film hinge 118 of this embodiment is designed to bend along substantially its entire length rather than at a single point or line. This helps the hinge resist fatigue or fracture better than film hinges that bend along a single line. The reinforcing c-glass fibers (and an optional filler) assist the elongate film hinge 118 in remaining elastic and flexible, which helps the hinge 118 to not become fatigued or broken after repeated bending.

The bracket embodiment illustrated in FIGS. 1A and 1B preferably includes an interactive cam structure 120 with a first curved surface 122 and a second curved surface 124. The first curved surface 122 interacts with the elongate film hinge 118 to provide a curved surface that helps ensure that the elongate film hinge 118 bends gradually over its entire length rather than abruptly at any specific locale. The second curved surface 122 is curved in such a way so that it interacts with a corresponding wall 125 of the base 110 so as to bias the ligation cover 112 toward an open position relative to the bracket base 110 when the ligation cover 112 is in the open position. This improves access to arch wire slot 114, making insertion or removal of the arch wire 116 easier. The second curved surface 124 may, depending on the shape of the corresponding wall 125 of the bracket base 110, also act to bias the ligation cover 112 to remain in a closed position when in the closed position relative to the bracket base 110.

An angled keyway 126 is provided near one end of the base 110. The ligation cover contains a corresponding locking tongue 128 that enables the ligation cover 112 to be selectively locked or unlocked relative to the bracket base 110. The ligation cover 112 is locked to bracket base 110 (as seen in FIG. 1B) by closing the ligation cover so that the locking tongue 128 is inserted into angled keyway 126.

In the event that the arch wire 116 pushes against the ligation cover with sufficient force to cause the cover to bulge upwardly relative to the bracket base 110, rather than causing the tongue 128 to withdraw from the angled keyway 126, which could result in undesired disengagement of the ligation cover, the locking tongue 128 is instead pulled more deeply into the angled keyway 126, thereby tightening the locking mechanism. This provides added safety, and in order to open the cover, the locking tongue 128 is pulled out of angled keyway 126 and over an outer protrusion 129 of the bracket base 110.

Furthermore, a bearing protrusion 130 is provided at the inside and middle of the ligation cover to assist in fixing the arch wire 116 in the slot 114 while the ligation cover is in the closed state (FIG. 1B). The bearing protrusion 130 reduces the play in the system by effectively widening the ligation cover 112 in the vicinity of the arch wire slot 114.

Figure 2A:
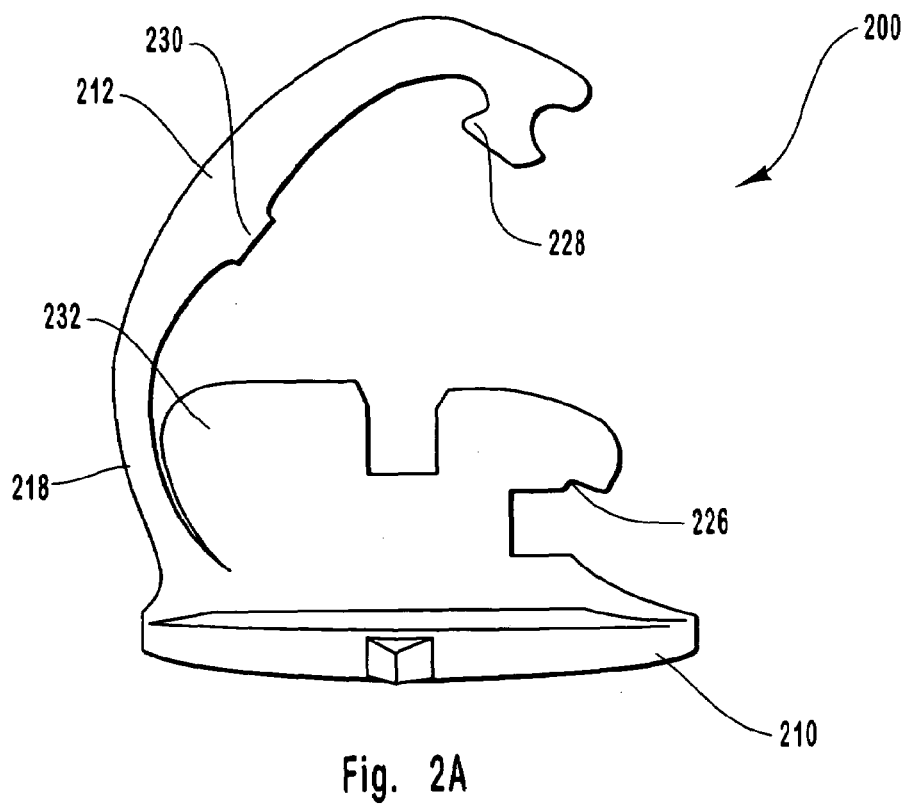
FIGS. 2A–2B illustrate an exemplary self-ligating orthodontic bracket that can be formed from a polymer resin reinforced with c-glass fibers, and/or glass particles.
Figure 2B:
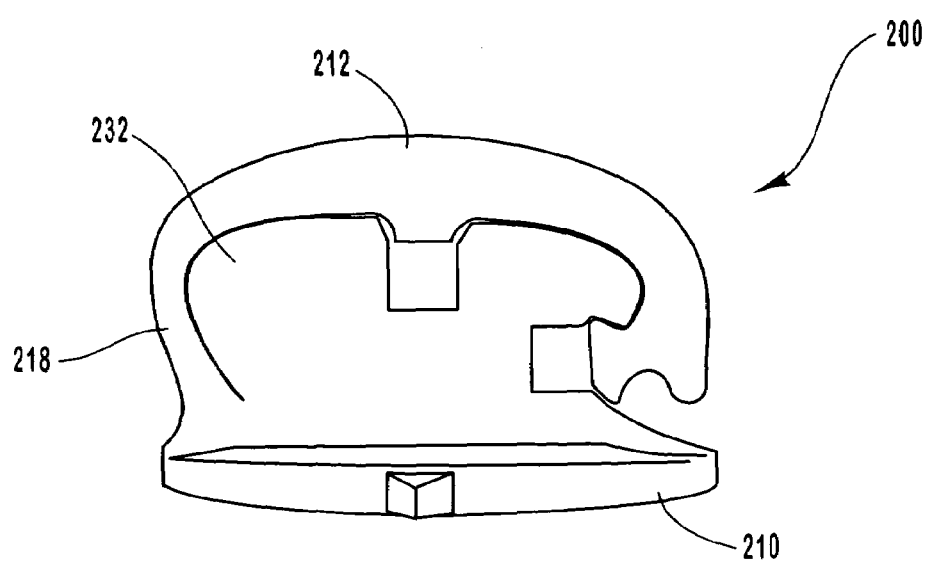

FIGS. 2A and 2B depict an alternative embodiment of an orthodontic bracket 200 according to the invention that does not include a cam structure. Instead, the orthodontic bracket 200 depicted in FIGS. 2A and 2B includes a bracket base 210 and a ligation cover 212 attached to the bracket base 210 by means of an elongate film hinge 218. The bracket also includes an angled keyway 226, a locking tongue 228, and a bearing protrusion 230. The bracket base 210 further includes a curved end 232 that acts as a hinge guide in order to cause the elongate film hinge 218 to bend gradually over a significant portion of its entire length. In this way, the curved end 232 of the bracket base 210 acts in similar manner to the curved hinge-guiding surface 122 of the cam structure 120 of the orthodontic bracket 100 depicted in FIGS. 1A–1B. Thus, as the ligation cover 212 is moved from an open, non-ligating position (FIG. 2A) to a closed, ligating position (FIG. 2B), the elongate film hinge 218 at least partially abuts the curved end 232. The abutment between the elongate film hinge 218 and the curved end 232 causes the elongate film hinge 218 to bend gradually around the curved end 232 so as to better distribute the bending forces and bending angles along substantially the entire length of the elongate film hinge 218.

Figure 3A:
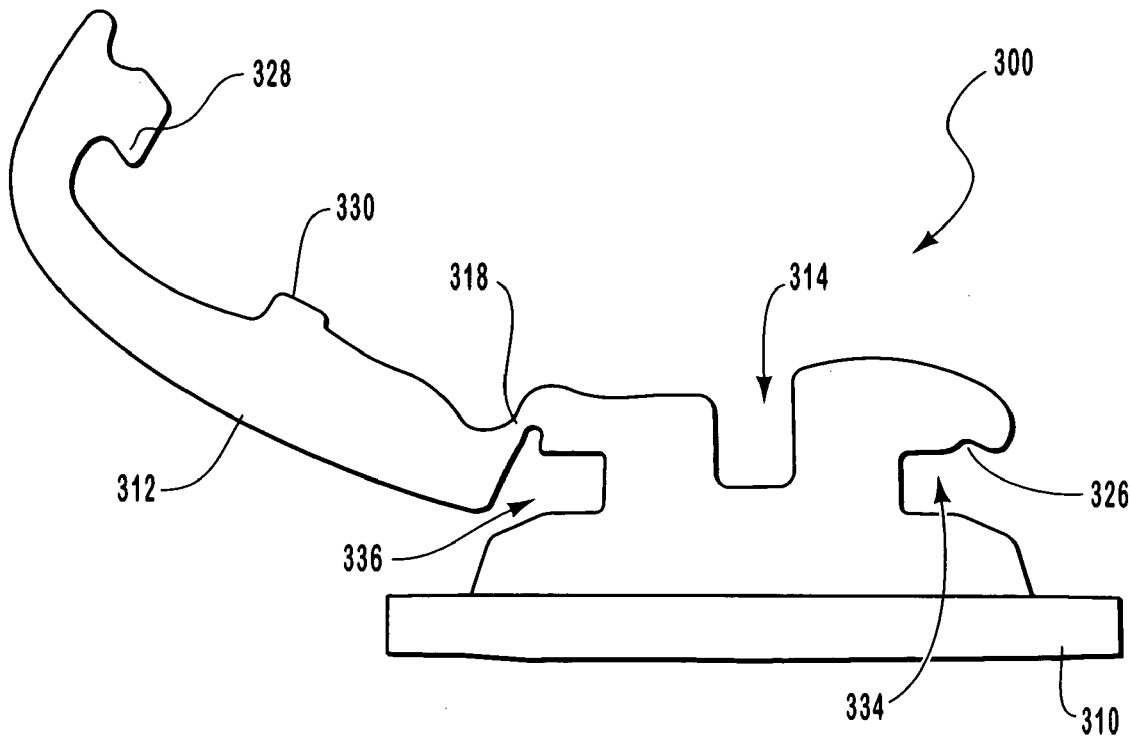
FIGS. 3A–3B illustrate an exemplary self-ligating orthodontic bracket that can be formed from a polymer resin reinforced with c-glass fibers and/or glass particles.
Figure 3B:
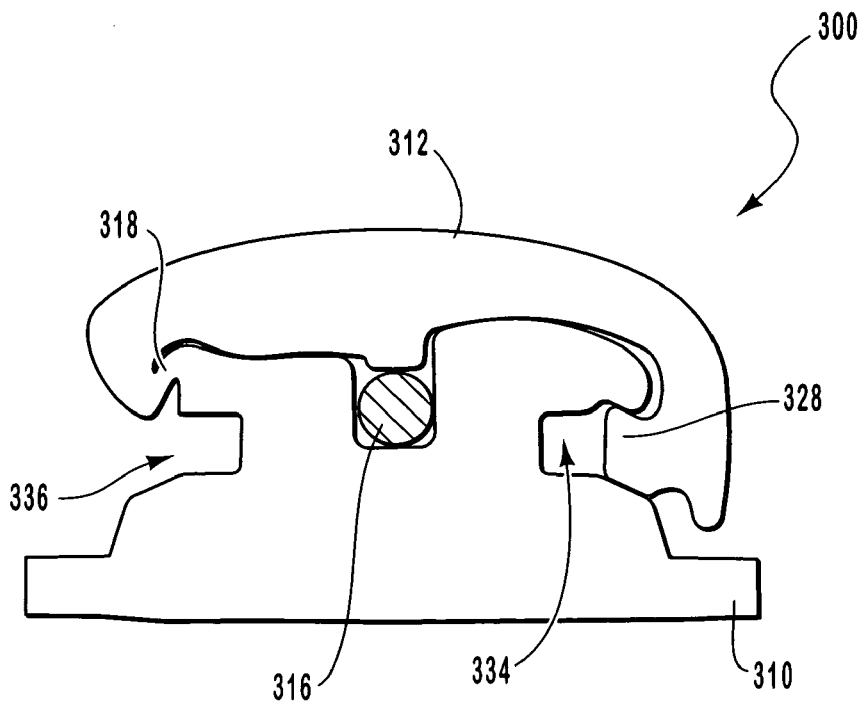

FIGS. 3A and 3B illustrate an alternative bracket embodiment that can also be formed from a polymer resin reinforced with c-glass fibers (and optionally a filler). Bracket 300 is similar to the bracket illustrated in FIGS. 1A–1B in that it includes a bracket base 310, a ligation cover 312, a slot 314, an arch wire 316 (seen in FIG. 3B), an angled keyway 326, a locking tongue 328, and a bearing protrusion 330. This example differs from the bracket illustrated in FIGS. 1A–1B in that although it also uses a film hinge 318 to attach the ligation cover 312 to the bracket base 310, the hinge 318 is not as elongate as hinge 118 shown in FIGS. 1A–1B. Bracket 300 may further include additional arch wire slots 334 and 336 for use with additional or alternative arch wires as known in the art. Reinforcing c-glass fibers provide overall increased strength and durability while providing increased flexibility and toughness in the region of the film hinge 318. Including both c-glass fibers and a glass particle filler provides even further increased flexibility, toughness, strength, and durability.

Figure 4A:
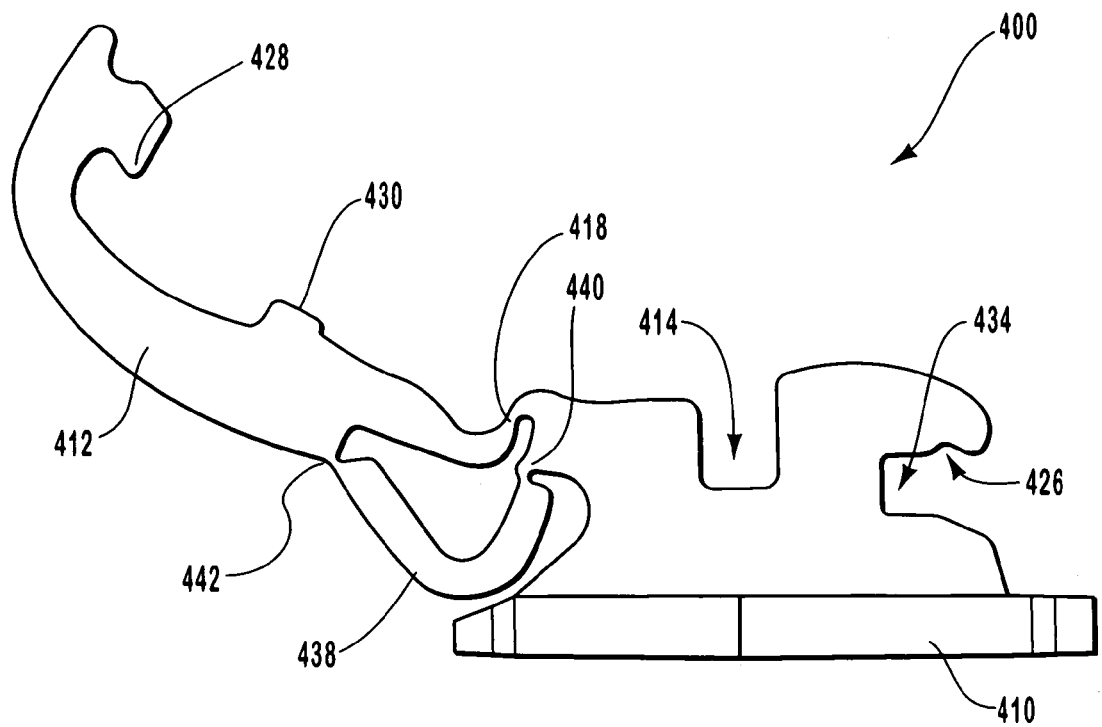
FIGS. 4A–4B illustrate an exemplary self-ligating orthodontic bracket that can be formed from a polymer resin reinforced with c-glass fibers and/or glass particles.
Figure 4B:
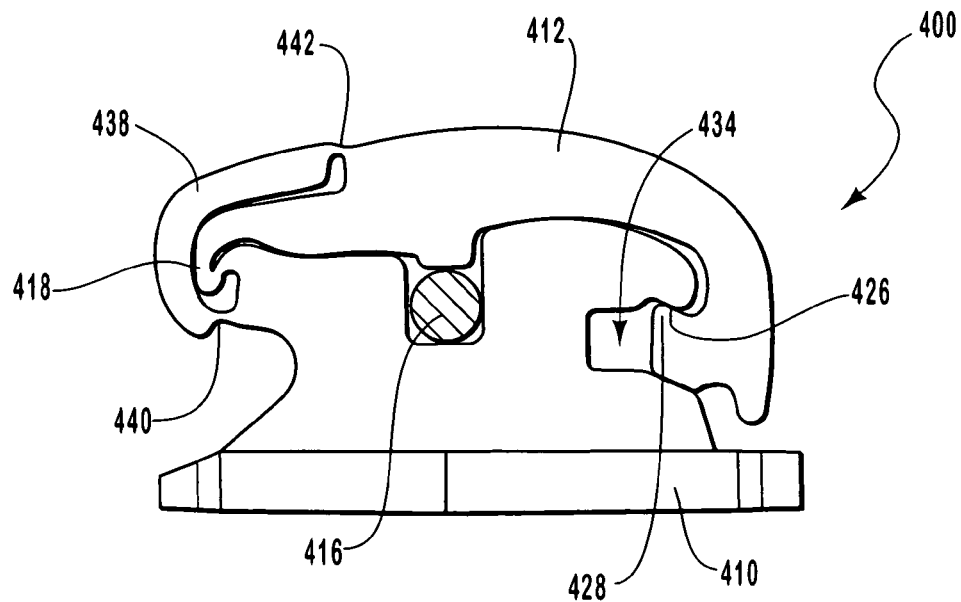

FIGS. 4A and 4B illustrate an alternative bracket embodiment that can also be formed from a polymer resin reinforced with c-glass fibers (and optionally a filler). Bracket 400 includes a bracket base 410, a ligation cover 412, a slot 414, an arch wire 416 (seen in FIG. 4B), a main film hinge 418, an angled keyway 426, a locking tongue 428, a bearing protrusion 430, and an additional arch wire slot 434. This example differs from that illustrated in FIGS. 3A–3B in that it further has a spring element 438 attached at one end of the bracket base 410 by a film hinge 440 and at an opposite end to the ligation cover 412 by a film hinge 442. Reinforcing c-glass fibers provide overall increased strength and durability while providing increased flexibility and toughness in the region of the film hinges 418, 440, 442, and spring element 438. Including both c-glass fibers and a glass particle filler provides even further increased flexibility, toughness, strength, and durability.

Various other bracket designs are disclosed in U.S. Pat. No. 6,607,383; U.S. application Ser. No. 09/914,737, filed Aug. 29, 2001, abandoned; and U.S. application Ser. No. 09/953,400, filed Sep. 12, 2001. For purposes of disclosing exemplary orthodontic bracket designs, the foregoing U.S. applications and patent are incorporated by reference.

The following comparative test results illustrate the advantages of forming an orthodontic bracket from a polymer resin reinforced with c-glass fibers, and the increased advantage of further including a glass particle filler.

EXAMPLE 1

An orthodontic bracket is formed by injection molding an acetal thermoplastic resin. The bracket design is the same as that illustrated in FIGS. 1A and 1B. No reinforcing glass fibers are used in molding the bracket. When used in an orthodontic procedure, the acetal thermoplastic polymer resin experiences deformation. In addition, although the hinge is very flexible, it is prone to breakage when a shearing force is applied to the ligation cover.

EXAMPLE 2

An orthodontic bracket is formed by injection molding an acetal thermoplastic resin reinforced with c-glass fibers. The bracket design is the same as that illustrated in FIGS. 1A and 1B. The concentration of c-glass fibers is 30% by weight of the overall bracket. When used in an orthodontic procedure, the c-glass reinforced orthodontic brackets better resists deformation than the bracket of Example 1. Moreover, the hinge is much stronger, and thus sufficiently flexible to bend repeatedly while opening and closing the ligation cover.

EXAMPLE 3

A hypothetical orthodontic bracket is formed by injection molding an acetal thermoplastic resin reinforced with c-glass fibers and glass spherical particle filler. The bracket design is the same as that illustrated in FIGS. 1A and 1B. The concentration of c-glass fibers is 35% by weight of the overall bracket. The concentration of glass particle filler is 10% by weight of the overall bracket, such that the total glass concentration (fibers plus filler) is 45% by weight. When used in an orthodontic procedure, the filled and c-glass reinforced orthodontic brackets better resist deformation than the brackets of Examples 1 and 2. Moreover, the hinge is even more durable than that of Example 2, and thus sufficiently flexible to bend repeatedly while opening and closing the ligation cover.

EXAMPLE 4

A hypothetical orthodontic bracket is formed by injection molding a nylon thermoplastic resin (e.g., TROGAMID or GRILAMID) reinforced with c-glass fibers. The bracket design is the same as that illustrated in FIGS. 1A and 1B. The concentration of c-glass fibers is 35% by weight of the overall bracket. When used in an orthodontic procedure, the hinge exhibits sufficient flexibility for use, although it is shows crazing after repeated opening and closing of the ligation cover. After many (e.g., 50) opening and closing cycles, the ligation cover will eventually separate from the bracket base.

EXAMPLE 5

A hypothetical orthodontic bracket is formed by injection molding a nylon thermoplastic resin (e.g., TROGAMID or GRILAMID) reinforced with c-glass fibers and glass spherical particle filler. The bracket design is the same as that illustrated in FIGS. 1A and 1B. The concentration of c-glass fibers is 35% by weight of the overall bracket. The concentration of glass particle filler is 10% by weight of the overall bracket, such that the total glass concentration (fibers plus filler) is 45% by weight. When used in an orthodontic procedure, the filled and c-glass reinforced orthodontic brackets are even more deformation resistant than the bracket of Example 4. Moreover, the hinge is even more durable than that of Example 4, and thus sufficiently flexible to bend repeatedly while opening and closing the ligation cover without crazing. Even after hundreds of opening and closing cycles, the ligation cover still remains attached to the bracket base.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthodontic bracket comprising:
   a bracket base;
   at least one arch wire slot in said bracket base, said slot being adapted to receive an arch wire therein; and
   a ligation cover hingedly connected to the bracket base by a hinge element and movable relative to the bracket base about the hinge element between an open, non-ligating position relative to the arch wire slot in which the arch wire slot is completely unoccluded by the ligation cover and a closed, ligating position relative to the arch wire slot;
   wherein the bracket base, hinge element, and ligation cover comprise a filled polymer resin composition reinforced with flexible glass or ceramic fibers and a particulate filler, wherein the hinge element reinforced with the flexible glass or ceramic fibers and the particulate filler has increased toughness and flexibility compared to a hinge element in the absence of the flexible glass or ceramic fibers and the particulate filler.

2. An orthodontic bracket as recited in claim 1, wherein the particulate filler comprises at least one of glass particles, ceramic particles, ceramic/glass particles, or organically modified ceramic particles.

3. An orthodontic bracket as recited in claim 2, wherein the particulate filler comprises spherical particles.

4. An orthodontic bracket as recited in claim 1, wherein the particulate filler is included in an amount in a range of about 1% to about 30% by weight of the polymer resin composition.

5. An orthodontic bracket as recited in claim 1, wherein the particulate filler is included in an amount in a range of about 2% to about 20% by weight of the polymer resin composition.

6. An orthodontic bracket as recited in claim 1, wherein to particulate filler is included in an amount in a range of about 5% to about 10% by weight of the polymer resin composition.

7. An orthodontic bracket as recited in claim 1, wherein to particulate filler includes particles having an average diameter in a range of about 0.3 to about 30 microns.

8. An orthodontic bracket as recited in claim 1, wherein the particulate filler includes particles having an avenge diameter in a range of about 0.5 to about 20 microns.

9. An orthodontic bracket as recited in claim 1, wherein the particulate filler includes particles having an avenge diameter in a range of about 1 to about 10 microns.

10. An orthodontic bracket as recited in claim 1, wherein the polymer resin composition is reinforced with c-glass fibers.

11. An orthodontic bracket as recited in claim 1, wherein the polymer resin comprises at least one of a polyetherimide, a polycarbonate resin, a polyaryletherketone resin, a polyamide resin, a crystalline polyamide, or an amorphous polyamide.

12. An orthodontic bracket as recited in claim 1, wherein the reinforcing fibers are included in an amount in a range of about 10% to about 50% by weight of the polymer resin composition.

13. An orthodontic bracket as recited in claim 1, wherein the reinforcing fibers are included in an amount in a range of about 15% to about 40% by weight of the polymer resin composition.

14. An orthodontic bracket as recited in claim 1, wherein the reinforcing fibers are included in an amount in a range of about 20% to about 35% by weight of the polymer resin composition.

15. An orthodontic bracket as recited in claim 1, wherein the bracket base and ligation cover are formed together as a single integral piece.

16. An orthodontic bracket comprising:
    a bracket base;
    at least one arch wire slot in said bracket base, said slot being adapted to receive an arch wire therein;
    a ligation cover hingedly connected to the bracket base and selectively rotatable relative to the bracket base between an open, non-ligating position and a closed, ligating position; and
    an elongate film hinge attached at one end to the bracket base and at an opposite end to the ligation cover so as to hingedly connect the ligation cover to the bracket base,
    wherein the bracket base, ligation cover, and film hinge comprise a polymer resin composition reinforced with substantially spherical filler particles comprising at least one of glass, ceramic, ceramic/glass, or organically modified ceramic particles, wherein the hinge element reinforced with the spherical filler particles has increased strength and flexibility compared to a hinge element in the absence of the substantially spherical filler particles.

17. An orthodontic bracket as recited in claim 16, wherein the filler particles comprise spherical glass particles.

18. An orthodontic bracket as recited in claim 16, wherein the polymer resin composition is further reinforced with at least one of glass or ceramic fibers.

19. An orthodontic bracket comprising:
    a bracket base;
    at least one arch wire slot in said bracket base, said slot being adapted to receive an arch wire therein; and
    a ligation cover hingedly connected to the bracket base and selectively rotatable relative to the bracket base about a hinge element between an open, non-ligating position in which the arch wire slot is completely unoccluded by the ligation cover and a closed-ligating position;
    wherein the bracket base, hinge element, and ligation cover comprise a polymer resin reinforced with spherical glass filler particles, wherein the hinge element reinforced with the spherical glass filler particles has increased strength and flexibility compared to a hinge element in the absence of the spherical glass filler particles.

20. An orthodontic bracket as recited in claim 19, wherein the polymer resin composition is further reinforced with al least one of glass or ceramic fibers.

* * * * *

UNITED STATES PATENT AND TRADEMARK OFFICE
CERTIFICATE OF CORRECTION

PATENT NO. : 7,063,530 B2
APPLICATION NO. : 11/071783
DATED : June 20, 2006
INVENTOR(S) : Abels et al.

It is certified that error appears in the above-identified patent and that said Letters Patent is hereby corrected as shown below:

Column 5
Line, 52, after "in an amount" remove "of"

Column 10
Line 49, remove "is"

Column 11
Line 57, change "avenge" to --average--
Line 60, change "avenge" to --average--

Column 12
Line 4, change "A n" to --An--
Line 63, change "al" to --at--

Signed and Sealed this

Twenty-ninth Day of May, 2007

JON W. DUDAS
*Director of the United States Patent and Trademark Office*